United States Patent
Quilliam (10) Patent No.: US 9,594,063 B2
(45) Date of Patent: Mar. 14, 2017

(54) RETENTION INDEX STANDARDS FOR LIQUID CHROMATOGRAPHY

(71) Applicant: National Research Council of Canada, Ottawa (CA)

(72) Inventor: Michael Arthur Quilliam, Bedford (CA)

(73) Assignee: National Research Council of Canada, Ottawa, Ontario ( * ) Notice: Subject to any disclaimer, the term of this patent is extended or adjusted under 35 U.S.C. 154(b) by 201 days.

(21) Appl. No.: 13/261,954

(22) PCT Filed: Mar. 15, 2013

(86) PCT No.: PCT/CA2013/000252
§ 371 (c)(1),
(2) Date: Sep. 12, 2014

(87) PCT Pub. No.: WO2013/134862
PCT Pub. Date: Sep. 19, 2013

(65) Prior Publication Data
US 2015/0140593 A1    May 21, 2015

Related U.S. Application Data

(60) Provisional application No. 61/611,760, filed on Mar. 16, 2012.

(51) Int. Cl.
*G01N 21/00* (2006.01)
*G01N 30/86* (2006.01)
(Continued)

(52) U.S. Cl.
CPC ......... *G01N 30/8668* (2013.01); *G01N 30/04* (2013.01); *G01N 30/8672* (2013.01);
(Continued)

(58) Field of Classification Search
None
See application file for complete search history.

(56) References Cited

U.S. PATENT DOCUMENTS 2,437,554 A    3/1948 Ratti et al.
3,006,822 A    10/1961 Todt et al.
(Continued)

FOREIGN PATENT DOCUMENTS

DE    10324149    12/2004
JP    9043199    2/1997
(Continued)

OTHER PUBLICATIONS

Ainsworth C, Benslay DN, Davenport J, Hudson JL, Kau D, Lin TM, Pfeiffer RR. (1967) Cholesterol-solubilizing agents related to the gallstone problem. J. Medicinal Chemistry. 10(2), 158-161.
(Continued)

*Primary Examiner* — Robert Xu
(74) *Attorney, Agent, or Firm* — Christian Berube (57) ABSTRACT

A homologous series of neutrally charged compounds having at least one functional group bearing a positive charge and at least one functional group bearing a negative charge are advantageous retention index standards for liquid chromatography, especially for liquid chromatography-mass spectrometry (LC-MS) methods, more especially for LC-MS methods employing electrospray (ESI) or atmospheric pressure chemical ionization (APCI) ionization systems.

10 Claims, 8 Drawing Sheets

(51) Int. Cl.
*G01N 30/04* (2006.01)
*G01N 30/72* (2006.01)

(52) U.S. Cl.
CPC ... *G01N 30/7233* (2013.01); *G01N 2030/042* (2013.01); *G01N 2030/045* (2013.01); *Y10T 436/10* (2015.01)

(56) References Cited

U.S. PATENT DOCUMENTS

| | | | |
|---|---|---|---|
| 3,336,324 | A | 8/1967 | Richter et al. |
| 3,444,056 | A | 5/1969 | Richter et al. |
| 4,120,859 | A | 10/1978 | Pluss et al. |
| 4,148,797 | A | 4/1979 | Pluss et al. |
| 4,501,673 | A | 2/1985 | Hodgson |
| 5,082,944 | A | 1/1992 | Losch et al. |
| 7,305,866 | B2 | 12/2007 | Kawana |
| 7,873,481 | B2 | 1/2011 | Walk et al. |

FOREIGN PATENT DOCUMENTS

| | | |
|---|---|---|
| JP | 2003139755 | 5/2003 |
| WO | 2004104571 A1 | 12/2004 |

OTHER PUBLICATIONS

Baker JK, Ma C-Y. (1979) Retention index scale for liquid-liquid chromatography. J. Chromatogr. 169, 107-115.

Bogusz M, Aderjan R. (1988) Improved standardization in reversed-phase high-performance liquid chromatography using 1-nitroalkanes as a retention index scale. J. Chromatogr. 435, 43-53.

Frisvad J, Thrane Ulf. (1987) Standardized high-performance liquid chromatography of 182 mycotoxins and other fungal metabolites based on alkylphenone retention indexes and UV-VIS spectra (diode array detection). J. Chromatogr. 404, 195-214.

Hill DW, Kelley TR, Langner KJ, Miller KW. (1984) Determination of mycotoxins by gradient high-performance liquid chromatography using an alkylphenone retention index system. Analytical Chemistry. 56, 2576-2579.

Kostiainen R, Kuronen P. (1991) Use of 1-[p-(2,3-dihydroxypropoxy)phenyl]-1-alkanones as retention index standards in the identification of trichothecenes by liquid chromatography-thermospray and dynamic fast atom bombardment mass spectrometry. J. Chromatogr. 543, 39-47.

Kuronen P. (1989) High-performance liquid chromatographic screening method for mycotoxins using retention indexes and diode array detection. Archives Environ. Contam. Toxicology. 18, 336-48.

International Search Report/Written Opinion for PCT/CA2013/000252 dated Jul. 3, 2013.

Smith RM. (1982) Alkyl aryl ketones as a retention index scale in liquid chromatography. J. Chromatogr. 236, 313-320.

Smith RM. (1995) Retention index scales used in high-performance liquid chromatography. Journal of Chromatography Library. 57, 93-144.

Yamauchi S, Mori, H. (1990) Phenols as internal standards in reversed-phase high-performance liquid chromatography in pharmaceutical analysis. J. Chromatogr. A. 515, 305-311.

Yamauchi S. (1993) Retention indices of phenols for internal standards in reversed-phase high-performance liquid chromatography. Application to retention prediction and selectivities of mobile phases and packing materials. J. Chromatogr. 635, 61-70.

Krokhin. O.V et al ••Peptide retention standards and hydrophobicity indexes in reversed-phase high-performance liquid chromatography of peptides . . . Analytical Chemistry. 81(22) 9522-9530. 2009.

RETENTION INDEX STANDARDS FOR LIQUID CHROMATOGRAPHY

CROSS-REFERENCE TO RELATED APPLICATIONS

This application is a national entry of International Patent Application PCT/CA2013/000252 filed Mar. 15, 2013 and claims the benefit of U.S. provisional patent application U.S. Ser. No. 61/611,760 filed 16 Mar. 2012, the entire contents of which are herein incorporated by reference.

FIELD OF THE INVENTION

The present invention relates to analytical chemistry, more particularly to liquid chromatography, especially liquid chromatography with mass spectrometry (LC-MS) and UV absorbance (LC-UV) detectors.

BACKGROUND OF THE INVENTION

Analytical methods based on high resolution liquid chromatography separation followed by mass spectrometry detection (LC-MS) or UV absorbance (LC-UV) detection are widely used for the analysis of a wide range of compounds such as biotoxins, drugs, persistent environmental pollutants, and other chemicals in wide range of samples such as plant and animal tissues, soil, water, etc. The identification of compounds present in samples is usually based on a match of both chromatographic retention time and mass or UV spectral data for authentic chemical standards with those of putative compounds observed in a sample. However, the absolute retention times of analytes can be highly variable between different laboratories and instruments, and even between days in the same laboratory. This usually requires the analysis of chemical reference standards on the same day each batch of samples is run to allow a good match of retention times for the conclusive identification of potential contaminants. This approach increases the workload of analysts and the cost of analyses. In addition, not every laboratory can stock all standards in order to accomplish this task as analysts may be concerned with the analysis of hundreds of possible analytes. It would be helpful to have a better way of cataloging retention data so that analytes can be more easily identified through a match of retention times without the use of in-house standards.

As an example, the above is particularly true with the analysis of marine and freshwater biotoxins. There are many different groups of biotoxins and within each group there can be many different structural analogues. Standards for many of these biotoxins are not commercially available and if they are, they can be very expensive. Analysts in this field face a difficult problem of determining which biotoxin analogues might be present in samples such as water, algae and shellfish. Similarly, for structural analogues or metabolites of pharmaceuticals and environmental pollutants, very few laboratories have ready access to standard compounds. This would be of concern to fields such as athlete doping control and monitoring of environmental samples and foodstuffs, among others.

Another issue of concern is related to the establishment of routine LC-MS analysis methods such as scheduled selected reaction monitoring, in which specific ion transitions are monitored over narrow windows that encompass the analytes of interest. The first step in setting up such a method is usually to perform an analysis of a mixture of all target analytes prior to establishing the windows. Again, the possible lack of every standard compound in a laboratory, as well as the extensive work required in this operation, presents problems to the analyst.

One way to correct for variations in retention data is to use "relative retention times (RRT)", in which analytes' retention times are measured relative to that of an internal standard compound. This method works fairly well in isocratic LC (constant solvent composition) but not in the more commonly-used gradient mode (changing solvent composition) because different LC instruments have different hold-up volumes in the gradient mixing system, which results in offsets in RRT values. The RRT values will also vary if there is any difference in the rate of change of the gradient slope or in column dimensions.

A better way to report retention data is to use "retention index (RI)" values. In this procedure, a series of homologous reference compounds are co-injected with the analytes. An interpolation of analyte retention times into a fitted curve of the plot of retention time vs. retention index value for the reference compounds results in a retention index value for each analyte.

The use of retention indices has been widely used in the field of gas chromatography. In this case, a series of n-alkanes is usually used as the RI standards and the resulting interpolated indices are usually referred to as "Kovats retention indices". This is possible because the commonly used flame ionization detector responds well to most organic compounds, including the n-alkanes, albeit that all the compounds must be volatile. These are not applicable to LC, especially LC-UV or LC-MS, because the n-alkanes are not easily detected by common UV or MS detectors.

Several different RI systems have been investigated by other researchers for use in LC-UV analysis (see Scheme 1).

Scheme 1 - Some retention index standards used in liquid chromatography.

These are most commonly used with the UV absorbance detector. These include Smith's work on alkyl aryl ketones (Smith R. M., (1982) *J. Chromatogr.* 236, 313-320; Smith R. M., (1995) *Journal of Chromatography Library* 57, 93-144), Baker and Ma's work on 2-ketoalkanes (Baker J. K., Ma C-Y., (1979) *J. Chromatogr.* 169, 107-115) and Bogusz and Aderjan's work on 1-nitroalkanes (Bogusz M., Aderjan R., (1988) *J. Chromatogr.* 435, 43-53). Two journal papers by one group alluded to the use of parabens (n-alkyl esters of 4-hydroxy benzoic acids) for measuring retention indices of phenols using LC-UV analysis (Yamauchi S., Mori, H., (1990) *J. Chromatogr. A.* 515, 305-311; Yamauchi S., (1993) *J. Chromatogr.* 635, 61-70). There have also been publications on application of LC-UV retention indices in the toxins field (Kuronen P., (1989) *Archives Environ. Contam. Toxicology* 18, 336-48; Frisvad J., Thrane U., (1987) *J. Chromatogr.* 404, 195-214; Hill D. W., Kelley T. R., Langner K. J., Miller K. W., (1984) *Analytical Chemistry* 56, 2576-2579). There has been only one publication on the use of retention indices for LC-MS (Kostiainen R., Kuronen P., (1991) *J. Chromatogr.* 543, 39-47) and this was based on 1-[p-(2,3-dihydroxypropoxyl)phenyl]-1-alkanones (Scheme 1) as retention index standards. However, the Kostiainen method uses a set of standards that are complicated to synthesize and not commercially available, but more importantly are not well suited to modern LC-MS methods based on electrospray (ESI) or atmospheric pressure chemical ionization (APCI).

Retention index standards of the prior art such as the alkylphenones were designed mainly for LC with UV absorbance detection. They are not well suited to LC-MS methods based on electrospray (ESI) or atmospheric pressure chemical ionization (APCI), the most commonly used ionization systems. In-studies carried out by the Inventors of the present invention, tests on alkylphenones as retention index standards in LC-MS show that the sensitivity of the alkylphenones in positive ion ESI is low, which requires more concentrated solutions to be injected which in turn results in bad peak shapes in the chromatograms. Also, they cannot be detected in the negative ion mode. Tests on parabens as retention index standards in LC-MS were more promising because they can be detected in negative ion mode but overall, their performance was lacking in terms of sensitivity and they still require high concentrations to be injected. In addition, there is potential susceptibility of the phenolic compounds to retention time changes due to variations in pH of the mobile phase, which can change the charge state of the parabens.

There remains a need for effective LC retention index standards, particularly for LC-MS methods.

SUMMARY OF THE INVENTION

It has now been found that a homologous series of neutrally charged compounds comprising at least one functional group bearing a positive charge and at least one functional group bearing a negative charge are advantageous retention index standards for liquid chromatography, especially for liquid chromatography-mass spectrometry (LC-MS) methods, more especially for LC-MS methods employing electrospray (ESI) or atmospheric pressure chemical ionization (APCI) ionization systems. The term "homologous series" is used to mean a group of compounds varying in structure only by the number of methylene groups in an alkyl chain.

Thus, there is provided a method of identifying an analyte of interest comprising: introducing the analyte of interest together with a series of homologous retention index standards into a liquid chromatography system, the retention index standards comprising neutrally charged compounds comprising at least one functional group bearing a positive charge and at least one functional group bearing a negative charge; assigning a retention index value to the analyte of Interest based on retention times and retention index values of the retention index standards; and, comparing spectral data and the retention index value of the analyte of interest to a library of spectral data and the retention index values for known compounds to identify the analyte of interest.

There is further provided use of a neutrally charged compound comprising at least one functional group bearing a positive charge and at least one functional group bearing a negative charge as a retention index standard in liquid chromatography.

There is further provided a series of retention index standards for use in liquid chromatography, the series of retention index standards comprising two or more neutrally charged homologous compounds, each compound comprising at least one functional group bearing a positive charge and at least one functional group bearing a negative charge. The term "series of retention standards" is used to mean a set of compounds varying in structure by the number of methylene groups in an alkyl chain, which variation results in different retention times.

There is further provided a use of the series of retention index standards in accordance with the present invention for creating a library of retention indices for reference compounds.

There is further provided a kit comprising a series of homologous compounds together with an indication or Instructions for their use as retention index standards in liquid chromatography, each homologous compound being a neutrally charged compound comprising at least one functional group bearing a positive charge and at least one functional group bearing a negative charge.

The neutrally charged compounds useful as retention index standards in the present invention have an overall neutral charge but bear individually charged functional groups. One or more of the individually charged functional groups bears a permanent positive charge while one or more bears a permanent negative charge provided the total charge of the compound is zero. Separation of charge between ionized functional groups within the compound advantageously enhances ionization and sensitivity in mass spectrometry in both the positive and negative ion modes. Further, compounds having permanently ionized functional groups and an overall neutral charge state will not vary with changes in mobile phase pH, thus making their retention times less sensitive to pH changes in the mobile phase.

Furthermore, the retention index (RI) standards used in the present invention are more polar than those currently being used, which results in quicker elution of the most polar members of the RI standards on the reverse-phase columns typically used in liquid chromatography methods. Earlier elution of the standards permits bracketing of polar analytes that are not bracketed by current non-polar standards, thereby extending the utility of the present retention index standards to a wider range of analytes.

The positively charged functional group preferably comprises a quaternary amine, tertiary amine, secondary amine, primary amine or imine group. Particularly preferred is a quaternary amine group. The negatively charged functional group preferably comprises a sulfonate, sulfate, phosphate, carboxyl, phenol, nitrate or arsenate group. Particularly preferred is a sulfonate group. In a preferred embodiment, the compound comprises a quaternary amine group and a sulfonate group. In a particularly preferred embodiment, the compound comprises a single quaternary amine group and a single sulfonate group.

In a preferred embodiment, the compounds are amine compounds of Formula (I):

(I)

where: m is an integer from 1 to 23; $R_1$ is H or $CH_3$; $R_2$ and $R_3$ are independently $C_{1-23}$ straight or branched chain alkyl group, or $R_2$ and $R_3$ taken together form a $C_{1-23}$ straight or branched chain alkyl imine group with the nitrogen atom, or $R_2$ and $R_3$ taken together form a 5- or 6-membered aromatic or aliphatic heterocyclic ring with the nitrogen atom; p is an integer from 1 to 23; and X is H or a sulfonate, sulfate, phosphate, carboxyl, phenol, nitrate or arsenate group; and that the compound comprises at least one of sulfonate, sulfate, phosphate, carboxyl, phenol, nitrate or arsenate group. Preferably, m is an integer from 1 to 17. Preferably, p is an integer from 1 to 17. Preferably, the length of straight or branched chain alkyl or straight or branched chain alkyl imine group is $C_{1-17}$.

The 5- or 6-membered aromatic or aliphatic heterocyclic ring may be substituted or unsubstituted. Where the ring possesses one or more substituents, the substituents are preferably independently sulfonate, sulfate, phosphate, carboxyl, phenol, nitrate, arsenate, $C_{1-23}$ straight or branched chain alkyl or $C_{1-23}$ straight or branched chain alkyl substituted by sulfonate, sulfate, phosphate, carboxyl, phenol, nitrate or arsenate. The ring is preferably a pyridine or piperidine ring, more preferably a pyridine ring. Compounds of Formula (I) are generally known in the art or can be synthesized from readily available starting materials using known procedures for the formation of amine and imine compounds.

In a particularly preferred embodiment, the compounds are 1-alkylpyridinesulfonic acids (APSAs). Some particularly preferred APSAs are compounds of Formula (II):

(II)

where n is an integer from 0 to 23, preferably from 0 to 17. The sulfonate group ($SO_3^-$) may be at the 2-, 3- or 4-position. Preferably, the sulfonate group ($SO_3^-$) group is at the 3-position. A series of homologous compounds of formula II means a set of compounds of formula II wherein only n is varied.

Compounds of Formula (II) may be synthesized by reacting a pyridinesulfonic acid (e.g., 3-pyridinesulfonic acid (CAS Registry Number: 636-73-7)) with n-alkyl halides $(CH_3(CH_2)_nL$, where n is as defined above and L is a leaving group, for example a halogen (e.g. Cl or Br). Some examples of APSAs are also known in the art, for example, C10 (n=9) and C12 (n=11) homologues (Ainsworth C., et al (1967) *J. Medicinal Chemistry* 10(2), 158-161) and C8 (n=7) to C24 (n=23) homologues (U.S. Pat. No. 4,148,797; U.S. Pat. No. 4,501,673). The N-methyl homologue (n=0) is commercially available. None of the known APSAs are known to be useful as retention index standards.

In the practice of the present invention, a series of homologous compounds useful as retention index standards in accordance with the present invention are introduced into an LC system together with one or more analytes of interest or a sample, for example by co-injection. If the instrument provides sufficient retention time reproducibility, then the retention index standards may also be injected in one run and the analytes of interest or a sample in a separate run. The retention index standards permit assignment of retention index (RI) values to the one or more analytes. Thus, a retention index (RI) value for each analyte may be obtained by interpolating analyte retention times into a fitted curve of the plot of retention time vs. retention index value for the retention index standards. The retention index value of the retention index standard is defined by the number of carbons in the longest alkyl chain in the molecule. There should be at least two retention index standards in the series, but more than two is preferable. Preferably, the number of retention index standards in the series should be in a range of from about 4 to 16 homologues. The series of homologous compounds used as the retention index standards preferably covers a wide range of masses to permit a good spread in retention times, thereby enabling effective bracketing of all analytes of interest and interpolation of retention times for a wider range of analytes. The RI values of the analytes of interest in a sample may be used in conjunction with spectral data (for example, mass spectrometry or UV absorbance data) on the same analytes to search a library (e.g., database) or libraries of retention indices and/or spectra of reference compounds for positive identification of known compounds in the sample.

The series of retention index standards may also be used to create libraries (e.g. databases) of retention indices for reference compounds for use in liquid chromatography analyses. Such libraries can be used not only for identifying analytes as discussed above, but also to predict retention times of the analytes on various columns using various gradient conditions and on different LC instruments. Documented retention indices for reference compounds in a library can facilitate the establishment of retention windows of targeted analytes in order to permit the programming of a scheduled selected reaction monitoring method. The process would involve first performing an analysis of a mixture of the retention index standards under the LC conditions and columns to be used for the sample. By interpolating the retention indices of the reference compounds in the library using a plot of retention time versus retention index for the retention index standards, the expected retention times of various reference compounds under the run conditions can be calculated.

The series of homologous compounds used as the retention index standards may be packaged into a kit together with an indication or instructions for their use as retention index standards in liquid chromatography. The compounds may be provided in the kit in separate containers and then mixed in desired proportions to be introduced with the analyte into the LC system. Preferably, the compounds are pre-prepared and included in the kit in ready-to-use mixtures of the retention index standards in solution.

The liquid chromatography (LC) system may be any suitable LC system. Liquid chromatography systems with mass spectrometry (LC-MS) or UV absorbance (LC-UV)

detectors are particularly preferred. The invention is particularly useful for liquid chromatography-mass spectrometry (LC-MS) methods, more particularly for LC-MS methods employing electrospray (ESI) or atmospheric pressure chemical ionization (APCI) ionization systems.

Analytes of Interest may be, for example, toxins (e.g., biotoxins or other poisons), pharmaceuticals, drugs of abuse, peptides, persistent environmental pollutants, food contaminants, or any other compound of interest. Of particular interest are marine and freshwater toxins as well as drugs used in aquaculture. Analytes may be from samples of any kind, for example, environmental samples (e.g.; water, soil and air), tissue samples (e.g., plant or animal tissues), bodily fluids (e.g., urine, blood, serum, semen), etc. Preparation of samples for use in LC methods may be accomplished by generally known procedures in the art.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
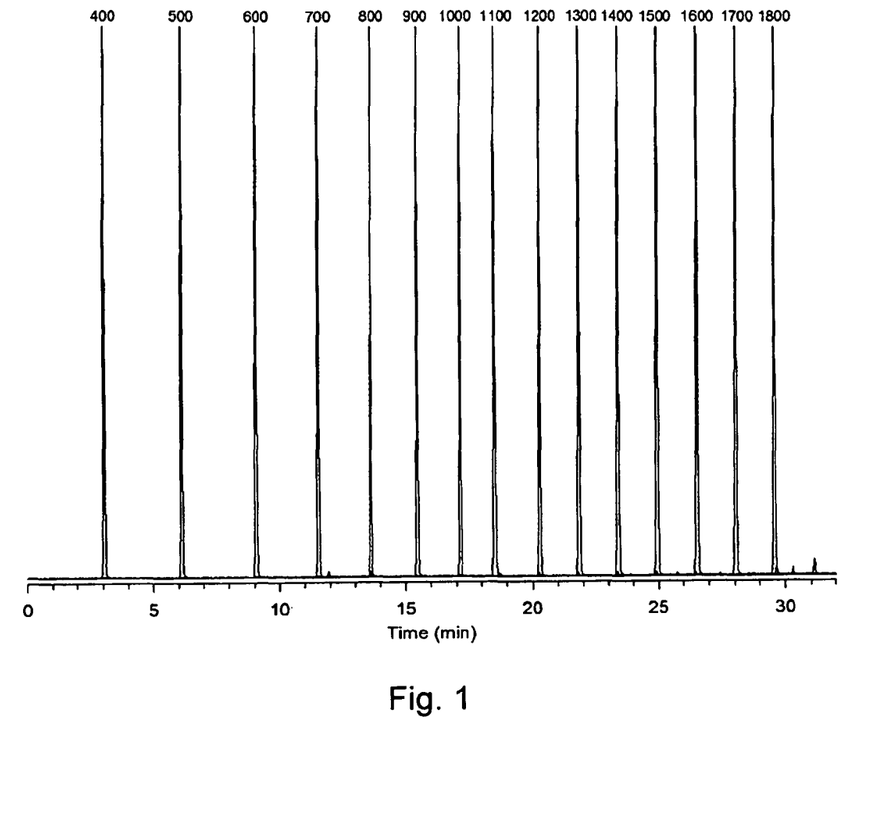
FIG. 1 depicts an LC-MS analysis of a 1-alkyl-3-pyridinesulfonic acid (APSA) mixture containing C4 to C18 homologues (compounds of Formula (I) where n=3-17)
Figure 2:
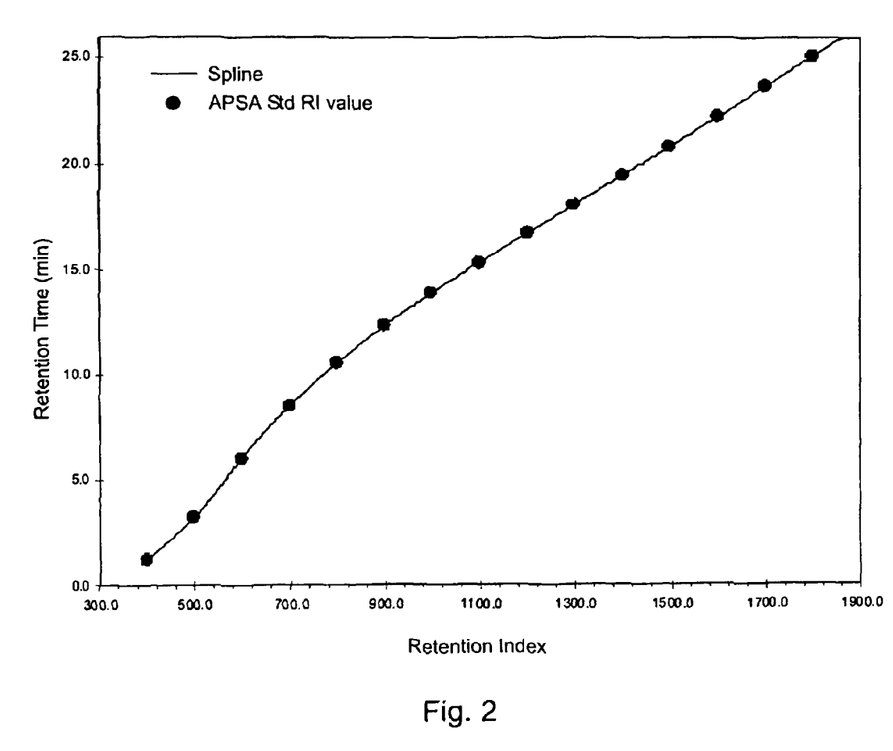
FIG. 2 depicts a spline fit graph for APSA standards with retention times of APSAs plotted against retention index value and fitted with a cubic spline curve.
Figure 3:
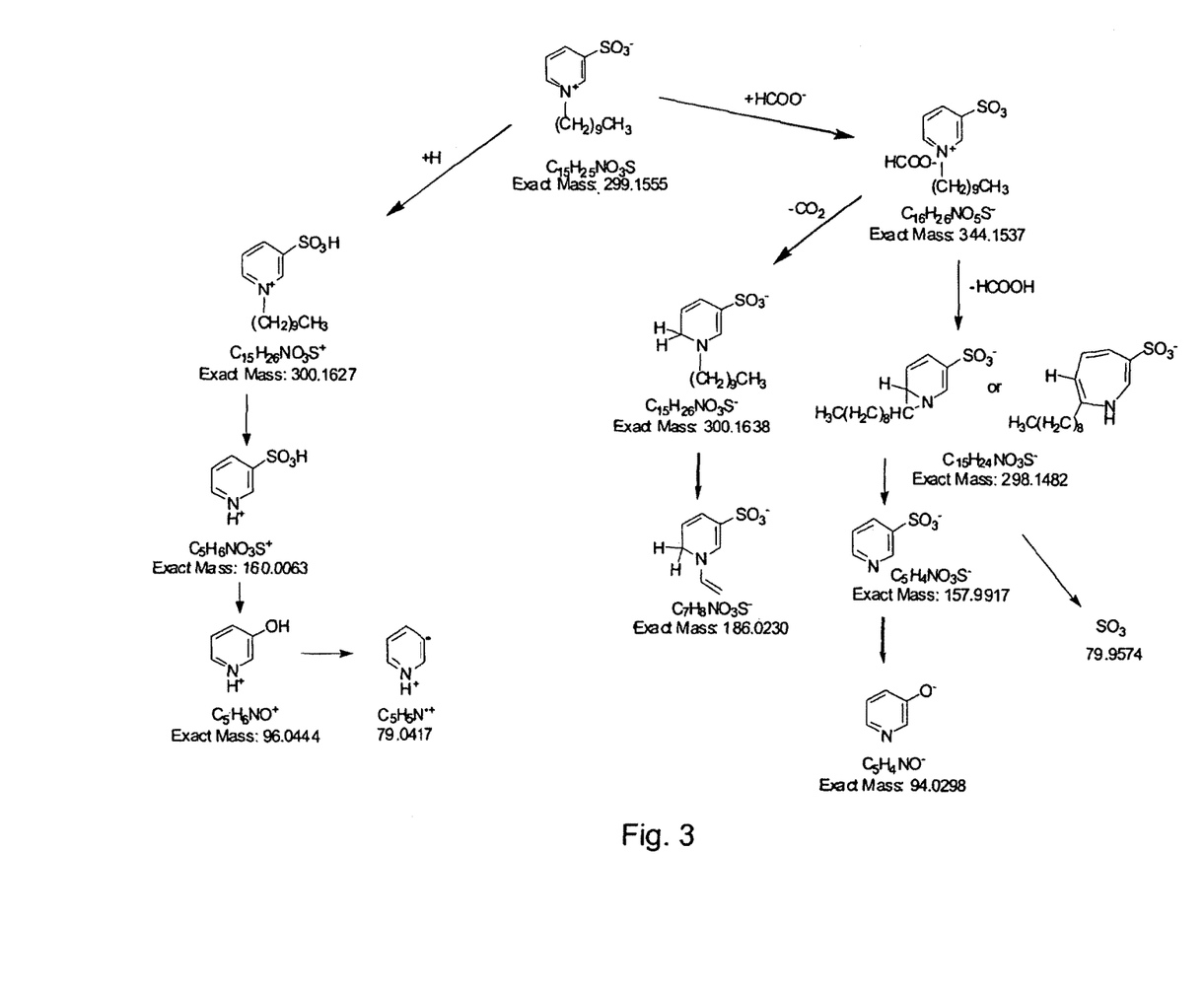
FIG. 3 depicts ionization and fragmentation characteristics of APSAs.

Referring to FIG. 1, an LC-MS analysis of a 1-alkyl-3-pyridinesulfonic acid (APSA) mixture containing C4 to C18 homologues demonstrates that APSAs give good chromatographic performance. With reference to FIG. 2, the plot of retention time vs. retention index for the APSA homologues gives a curve that is well-fitted by a cubic spline. Retention index is defined as the number of carbons in the side chain of the APSA multiplied by 100. The APSA compounds give excellent response in mass spectrometric detection using either positive or negative ion modes. Selected reaction monitoring (SRM) can be used to monitor the compounds as they all fragment to the same product ion (m/z 160 in positive mode and m/z 158 in negative mode) (see FIG. 3). The compounds also have an excellent UV chromophore with an absorbance maximum at 266 nm, so they can be used as retention index markers in LC-UV analyses as well.

Example 1

Use of APSA Retention Index Standards to Identify Microcystins by LC-MS

Figure 4:
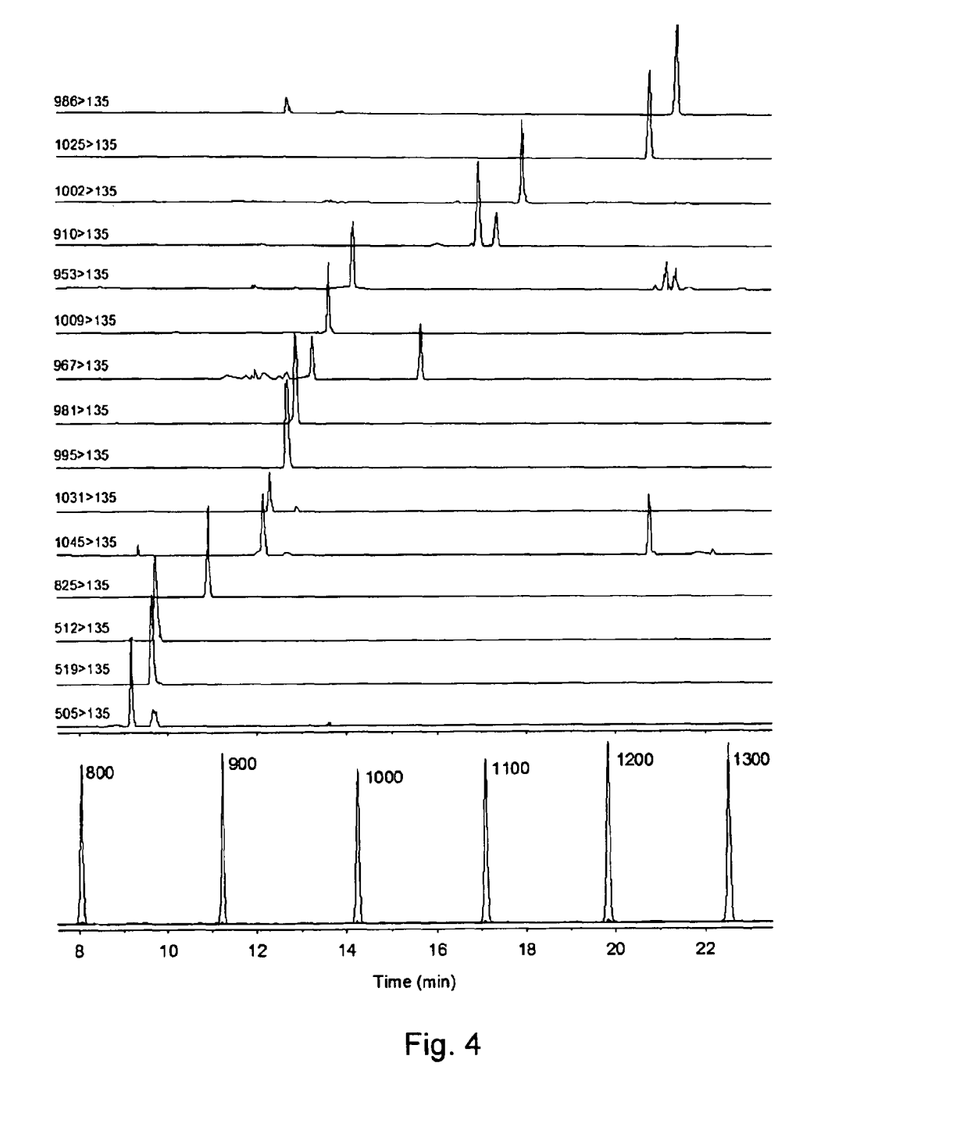
FIG. 4 depicts LC-MS analysis of a cyanobacterial extract containing microcystins co-injected with a mixture of APSA standards, in which: upper plots show signals for targeted microcystins (not all the analyte peaks labeled) and bottom plot shows signals for the APSA standards (the APSA peaks labeled with their retention index numbers, 400 to 1800)

A sample of cyanobacterial extract containing analytes of Interest (i.e. microcystins) was co-injected with a mixture of the C4-C18 APSA standards into a reversed phase liquid chromatography-mass spectrometry system. The system comprises an LC-ESI-QqQ (QTRAP 4000) instrument with an Agilent 2.7 μm-Poroshell 120 Å SB-C18 column (2.1× 150 mm). Elution conditions comprise mobile phase: A=water, B=MeCN/water (95:5), both with 50 mM formic acid+2 mM ammonium hydroxide at pH 2.2; with a gradient of 25-75% B over 30 min at a hold time of 5 min, flow rate of 0.25 ml/min, and column temperature of 40° C. The liquid chromatography (LC) column provides separation of the complex mixture while the mass spectrometer provides detection of both the microcystins within the sample and the co-injected APSA standards (FIG. 4). The characteristic mass spectral signals and the retention times of the microcystins and APSAs in the sample are measured. In FIG. 4, the top box shows the signals for targeted microcystins, while the bottom box shows signals for the APSA standards. The APSA peaks are labeled with their retention index numbers, 400 to 1800.

Figure 5:
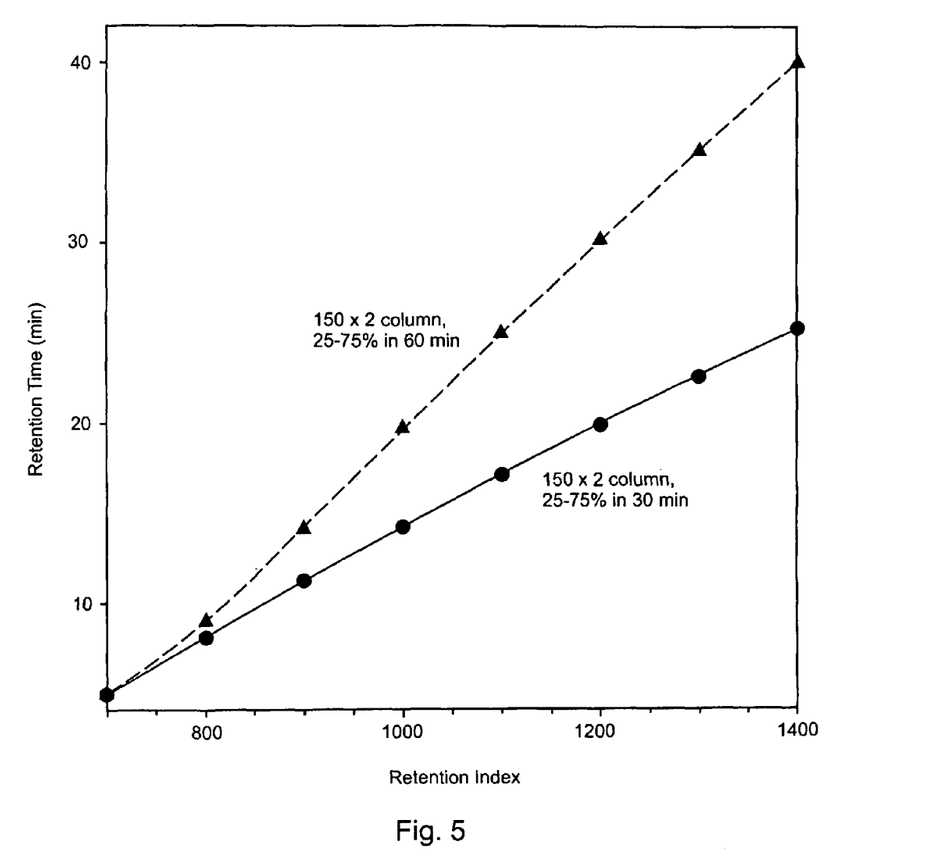
FIG. 5 depicts a plot of retention time vs. retention index value for APSA standards observed in the LC-MS analysis shown in FIG. 4 (circles and solid trace) and for a separate analysis (triangles and dashed trace) on the same LC column but with a 60 min gradient rather than the 30 min used in FIG. 4.

An interpolation of microcystin retention time into a fitted curve of the plot of retention time versus retention index value for the APSAs (FIG. 5) results in a measured retention index for the microcystins. In FIG. 5, the plot with circles and solid trace is for the LC-MS analysis shown in FIG. 4 (30 min gradient), while the plot with triangles and dashed trace is a separate analysis on the same LC column under the same conditions but with a 60 min gradient rather than a 30 min gradient. The curve fitting is best done using the method of cubic splines, and FIG. 5 shows the cubic spline fits generated to fit both sets of data.

The resulting retention index of the analyte of interest, as well as its mass spectral data, can then be compared to a database previously established for a wide range of analytes in order to identify the analyte of interest. In the present example, the sample contains more than one analyte of interest (i.e., multiple microcystins) and the method generates a list of analytes identified in the sample (Tables 1a-1c).

TABLE 1a

| | Short gradient (25-75% B, 30 min) | | | | |
|---|---|---|---|---|---|
| Microcystin Code | Precursor Ion > 135 | RT (min) | Average RIa | 1 day SD (n = 5) | 4 day SD (n = 5, d = 4) |
| 3dm7dmRR | 505.8 | 9.17 | 832.6 | 0.4 | 0.5 |
| RR | 519.8 | 9.64 | 847.2 | 0.3 | 0.8 |

TABLE 1a-continued

Short gradient (25-75% B, 30 min)

| Microcystin Code | Precursor Ion > 135 | RT (min) | Average RIa | 1 day SD (n = 5) | 4 day SD (n = 5, d = 4) |
|---|---|---|---|---|---|
| 7dmRR | 512.8 | 9.72 | 850.4 | 0.4 | 0.7 |
| Nod-R | 825.5 | 10.91 | 888.7 | 0.5 | 0.7 |
| YR | 1045.6 | 12.12 | 929.3 | 0.4 | 0.6 |
| 7dmYR | 1031.6 | 12.30 | 934.1 | 0.4 | 0.7 |
| LR | 995.6 | 12.69 | 946.7 | 0.1 | 1.3 |
| 7dmLR | 981.6 | 12.87 | 953.3 | 0.3 | 1.3 |
| 3dm7dmLR | 967.6 | 13.24 | 965.6 | 0.4 | 1.2 |
| (O—Me)LR | 1009.9 | 13.61 | 977.8 | 0.5 | 1.3 |
| 7dmHilR | 995.6 | 13.82 | 985.2 | 0.8 | 0.9 |
| RA | 953.8 | 14.16 | 995.3 | 0.6 | 2.1 |
| LA | 910.6 | 16.93 | 1092.5 | 0.2 | 2.4 |
| isoLA | 910.6 | 17.35 | 1106.8 | 0.3 | 2.9 |
| LY | 1002.9 | 17.91 | 1128.3 | 0.4 | 1.8 |
| LW | 1025.9 | 20.77 | 1232.9 | 0.2 | 1.8 |
| LF | 986.8 | 21.38 | 1255.1 | 0.3 | 2.4 |

TABLE 1b

Long gradient (25-75% B, 60 min)

| Microcystin Code | Precursor Ion > 135 | RT (min) | Average RIb | 1 day SD (n = 5) | 4 day SD (n = 5, d = 4) |
|---|---|---|---|---|---|
| 3dm7dmRR | 505.8 | 11.33 | 842.3 | 0.7 | 1.2 |
| RR | 519.8 | 12.18 | 858.4 | 0.5 | 1.5 |
| 7dmRR | 512.8 | 12.32 | 862.0 | 0.3 | 1.2 |
| Nod-R | 825.5 | 14.29 | 901.3 | 0.2 | 1.1 |
| YR | 1045.6 | 16.75 | 947.0 | 0.4 | 0.8 |
| 7dmYR | 1031.6 | 17.01 | 952.1 | 0.5 | 0.8 |
| LR | 995.6 | 17.75 | 964.9 | 0.2 | 1.6 |
| 7dmLR | 981.6 | 18.19 | 972.9 | 0.2 | 1.9 |
| 3dm7dmLR | 967.6 | 18.85 | 984.7 | 0.5 | 1.3 |
| (O—Me)LR | 1009.9 | 19.59 | 997.6 | 0.4 | 1.5 |
| 7dmHilR | 995.6 | 19.94 | 1004.5 | 0.5 | 1.4 |
| RA | 953.8 | 20.45 | 1012.8 | 0.2 | 2.3 |
| LA | 910.6 | 25.63 | 1110.0 | 0.4 | 2.8 |
| isoLA | 910.6 | 26.39 | 1124.4 | 0.2 | 3.0 |
| LY | 1002.9 | 27.68 | 1150.4 | 0.2 | 1.9 |
| LW | 1025.9 | 33.20 | 1259.1 | 0.5 | 1.9 |
| LF | 986.8 | 34.25 | 1280.6 | 0.4 | 2.5 |

TABLE 1c 2-point correction of (b) to match (a)

| Microcystin Code | Precursor Ion > 135 | RIc | % Diff. to (a) |
|---|---|---|---|
| 3dm7dmRR | 505.8 | 831.6 | -0.11 |
| RR | 519.8 | 847.2 | 0.00 |
| 7dmRR | 512.8 | 850.8 | 0.04 |
| Nod-R | 825.5 | 888.9 | 0.03 |
| YR | 1045.6 | 933.3 | 0.42 |
| 7dmYR | 1031.6 | 938.3 | 0.44 |
| LR | 995.6 | 950.7 | 0.41 |
| 7dmLR | 981.6 | 958.4 | 0.53 |
| 3dm7dmLR | 967.6 | 969.9 | 0.43 |
| (O—Me)LR | 1009.9 | 982.4 | 0.46 |
| 7dmHilR | 995.6 | 989.0 | 0.38 |
| RA | 953.8 | 997.1 | 0.18 |
| LA | 910.6 | 1091.0 | -0.13 |
| isoLA | 910.6 | 1104.8 | -0.18 |
| LY | 1002.9 | 1129.9 | 0.14 |
| LW | 1025.9 | 1234.5 | 0.12 |
| LF | 986.8 | 1255.1 | 0.00 |

Table 1a provides retention times (RT) and retention indices (RI) measured for the microcystins detected in the LC-MS analysis shown in FIG. 4 (30 min gradient). Excellent reproducibility data for analyses is shown for within-day (number of runs, n=5) and between-day (number of days, d=4) runs. Also shown is data using the same column but with a 60 min gradient (Table 1b). Finally, in Table 1c, the data from the 60 min gradient (Table 1b) has been adjusted to match the 30 min gradient data (Table 1a) using a 2-point correction based upon the retention data for two microcystins, RR and LF. This process allows fine tuning of the matching of data and results in less than 1% difference is observed for the corrected 60 min RI data vs. the 30 min RI data (Table 1c).

Example 2

Figure 6:
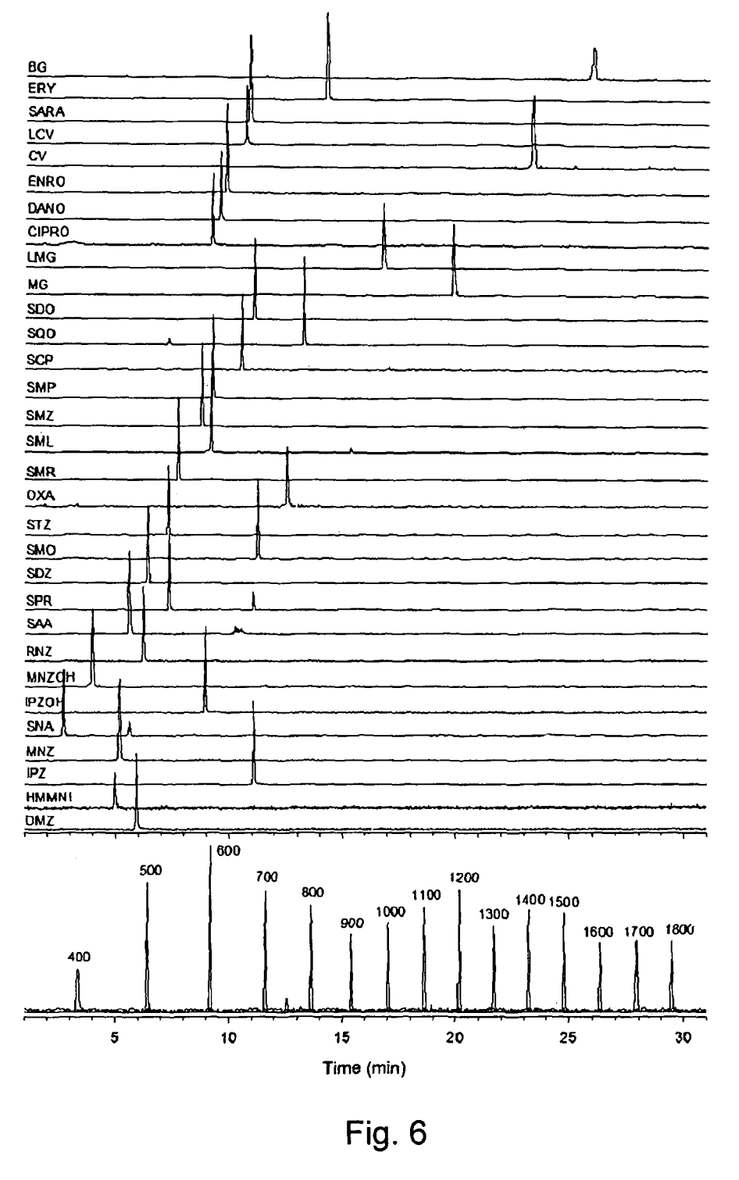
FIG. 6 depicts LC-MS analysis of a mixture of reference standards of various drugs that are routinely monitored by food inspection agencies because of their, use in agriculture and aquaculture.

Use of APSA Retention Index Standards to Establish a Database of Retention Indices of Analytes for LC-MS A solution containing various reference compounds (i.e. drugs that have been used in agriculture and aquaculture and that are routinely monitored by food inspection agencies) is co-injected along with a mixture of the C4-C18 APSA standards into a reversed phase liquid chromatography-mass spectrometry system. The system comprises an LC-ESI-QqQ (QTRAP 4000) instrument with an Agilent 2.7 µm-Poroshell 120 Å SB-C18 column (2.1×150 mm). Elution conditions comprise mobile phase: A=water, B=MeCN/water (95:5), both with, 50 mM formic acid+5 mM ammonium hydroxide at pH 2.2; with a gradient of 5-100% B over 30 min at a hold time of 5 min, flow rate of 0.25 ml/min, and column temperature of 35° C. The liquid chromatography (LC) column provides separation of the complex mixture while the mass spectrometer provides detection of both the reference compounds and the co-injected APSA standards. The characteristic retention times of the reference compounds and the APSAs are measured. FIG. 6 depicts the LC-MS analysis of the mixture of reference compounds and co-injected APSA standards. The upper plots show the signals for drugs (not all the drug peaks are labeled) while the bottom plot shows the signals for the APSA standards that were co-injected with drugs.

Figure 7:
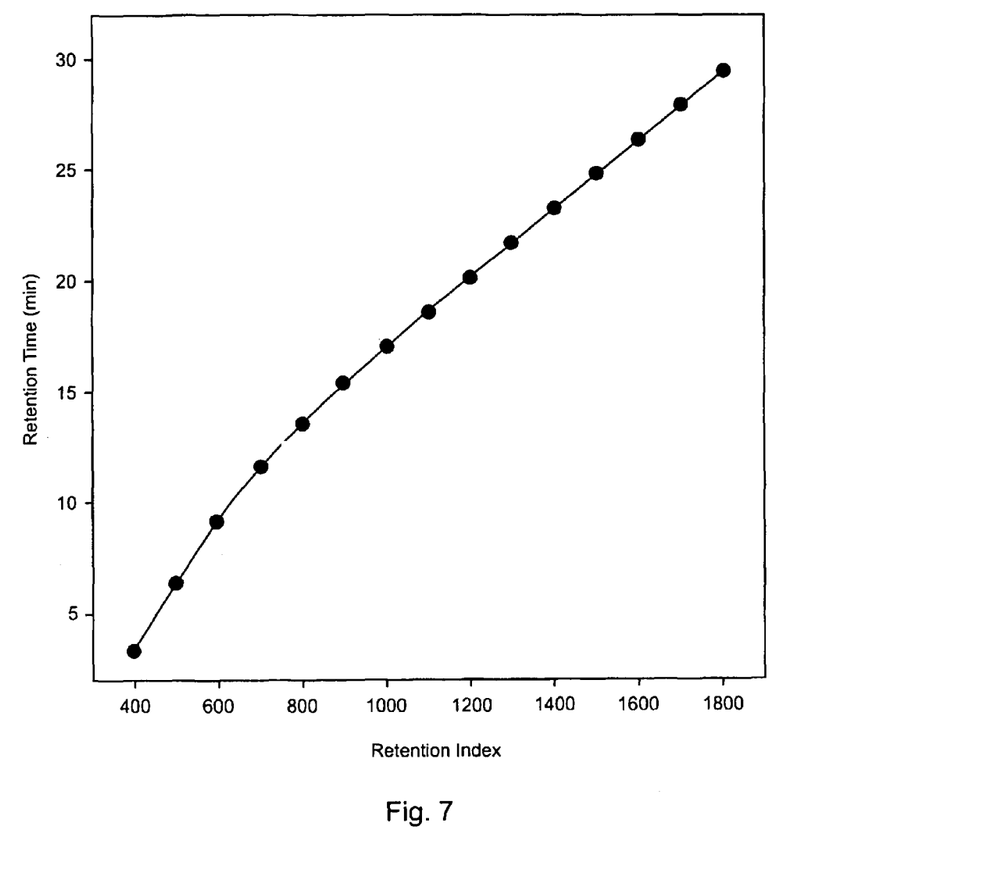
FIG. 7 depicts a plot of the retention times vs. retention index values for APSA standards observed in the LC-MS analysis shown in FIG. 6, with a cubic spline fit generated to fit the data; and, FIG. 8 depicts a plot of the retention times vs. retention index values for APSA standards measured in three different LC-MS analyses using two different columns (150 vs. 50 mm length) and two different gradients, with cubic spline fits generated to fit the data.

An interpolation of the retention times of the reference compounds into a fitted curve of the plot of retention time versus retention index value for the APSAs (FIG. 7) results in a measured retention index for the reference compounds. The curve fitting is done using the method of cubic splines. The resulting retention index of the reference compounds are then entered into a database, for example Table 2. Table 2 provides a listing of the reference compounds analyzed in FIG. 6 along with their measured retention times (RT) and calculated retention indices (RI). The standard deviation (SD) value shows the excellent reproducibility measured from 5 repeat analyses on the same day.

TABLE 2

| Name of Compound | Abbrev | SRM transition | Avg. RT (min) | Avg. RI | SD (n = 5) RI |
|---|---|---|---|---|---|
| Sulfonamides | | | | | |
| Sulfanilamide | SNA | 173.1 > 92.1 | 2.70 | 379.7 | 1.3 |
| Sulfacetamide | SAA | 215.1 > 156.1 | 5.58 | 471.9 | 0.6 |
| Sulfadiazine | SDZ | 251.1 > 156.1 | 6.42 | 500.1 | 0.4 |
| Sulfathiazole | STZ | 256.1 > 156.1 | 7.29 | 530.4 | 0.4 |
| Sulfapyridine | SPR | 250.1 > 156.1 | 7.34 | 531.9 | 0.2 |
| Sulfamerazine | SMR | 265.1 > 92.1 | 7.75 | 546.8 | 0.4 |
| Sulfamethazzine | SMZ | 279.1 > 186.1 | 8.76 | 584.0 | 0.3 |
| Sulfamethizole | SML | 271.1 > 156.1 | 9.19 | 600.3 | 0.2 |
| Sulfamethoxypyridazine | SMP | 281.1 > 126.1 | 9.25 | 602.9 | 0.2 |
| Sulfachloropyridazine | SCP | 285.1 > 156.1 | 10.52 | 653.9 | 0.3 |
| Sulfadoxine | SDO | 311.1 > 156.1 | 11.07 | 676.9 | 0.3 |
| Sulfamethoxazole | SMO | 254.1 > 156.1 | 11.25 | 685.1 | 0.2 |
| Sulfaquinoxaline | SQO | 301.1 > 156.1 | 13.24 | 780.4 | 0.2 |
| Nitroimidazoles | | | | | |
| 1-(2-Hydroxyethyl)-2-hydroxymethyl-5-nitroimidazole | MNZ-OH | 188.1 > 123.1 | 3.95 | 419.5 | 0.5 |
| 2-Hydroxymethyl-1-methyl-5-nitrimidazole | HMMNI | 158.1 > 140.1 | 5.00 | 453.1 | 0.2 |
| Metronidazole | MNZ | 172.1 > 128.1 | 5.13 | 457.3 | 0.5 |
| Dimetridazole | DMZ | 142.1 > 96.1 | 5.90 | 482.6 | 0.3 |
| Ronidazole | RNZ | 201.1 > 55.1 | 6.22 | 493.3 | 0.4 |
| 1-Methyl-2-(2'-hydroxyisopropyl)-5-nitroimidazole | IPZ-OH | 186.1 > 168.1 | 8.93 | 590.6 | 0.2 |
| Ipronidazole | IPZ | 170.1 > 109.1 | 11.07 | 676.9 | 0.4 |
| Fluoroquinolones | | | | | |
| Ciprofloxacin | CIPRO | 332.2 > 245.1 | 9.20 | 601.0 | 0.2 |
| Danofloxacin | DANO | 358.2 > 96.1 | 9.54 | 614.1 | 0.3 |
| Enrofloxacin | ENRO | 360.2 > 316.2 | 9.82 | 625.2 | 0.4 |
| Sarafloxacin | SARA | 386.2 > 342.2 | 10.82 | 666.2 | 0.3 |
| Quinolones | | | | | |
| Oxolinic acid | OXA | 262.1 > 216.1 | 12.53 | 744.6 | 0.6 |
| Macrolides | | | | | |
| Erythromycin | ERY | 734.5 > 158.1 | 14.23 | 833.3 | 0.6 |
| Dyes | | | | | |
| Leucocrystal Violet | LCV | 374.4 > 358.1 | 10.68 | 660.3 | 0.6 |
| Leucomalachite green | LMG | 331.1 > 316.1 | 16.76 | 983.2 | 0.9 |
| Malachite Green | MG | 329.2 > 313.1 | 19.84 | 1180.8 | 1.2 |
| Crystal Violet | CV | 372.4 > 356.1 | 23.31 | 1406.5 | 1.1 |
| Brilliant Green | BG | 385.3 > 341.1 | 25.90 | 1572.6 | 1.0 |

Example 3

Use of APSA Retention Index Standards to Predict Retention Times for Analytes in Order to Establish Windows for Scheduled SRM Analysis by LC-MS A database of retention indices for reference compounds (e.g., Table 2) is used to predict retention times of the same compounds that are to be run on columns with different dimensions, possibly with using various gradient conditions or different LC instruments. This can facilitate the establishment of retention windows of targeted analytes in order to permit the programming of a scheduled selected reaction monitoring method. The process involves first performing an analysis of a mixture of the APSA retention index standards under the LC conditions and on the column and instrument to be used for samples. Interpolation of the database retention indices for reference compounds into a plot of the retention times vs. retention index values for APSA standards would allow the calculation of retention times expected under those new conditions.

Figure 8:
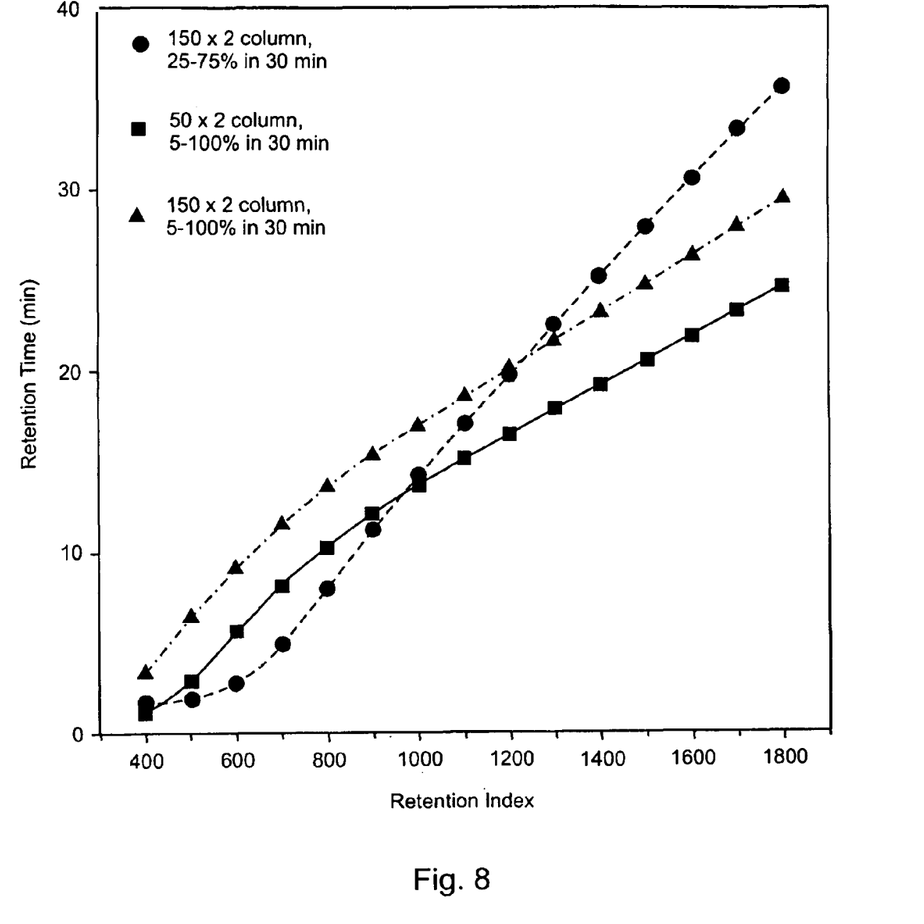

FIG. 8 depicts a plot of the retention time vs. retention index values for APSA standards measured in three different LC-MS analyses using two different columns (150 vs 50 mm length) and two different gradients. A cubic spline fit has been generated to fit the data. Table 3 presents the prediction of drug retention times on a 50×2 mm column using the retention indices documented in in Table 2 and the plot shown in FIG. 8.

TABLE 3

| Drug Class | Name of Compound | Abbrev | SRM transition | Database RI | Predicted RT (min) |
|---|---|---|---|---|---|
| Sulfonamides | Sulfanilamide | SNA | 173.1 > 92.1 | 379.7 | 0.8 |
| | Sulfacetamide | SAA | 215.1 > 156.1 | 471.9 | 2.3 |

TABLE 3-continued

| Drug Class | Name of Compound | Abbrev | SRM transition | Database RI | Predicted RT (min) |
|---|---|---|---|---|---|
| | Sulfadiazine | SDZ | 251.1 > 156.1 | 500.1 | 2.9 |
| | Sulfathiazole | STZ | 256.1 > 156.1 | 530.4 | 3.7 |
| | Sulfapyridine | SPR | 250.1 > 156.1 | 531.9 | 3.7 |
| | Sulfamerazine | SMR | 265.1 > 92.1 | 546.8 | 4.1 |
| | Sulfamethazzine | SMZ | 279.1 > 186.1 | 584.0 | 5.2 |
| | Sulfamethizole | SML | 271.1 > 156.1 | 600.3 | 5.6 |
| | Sulfamethoxypyridazine | SMP | 281.1 > 126.1 | 602.9 | 5.7 |
| | Sulfachloropyridazine | SCP | 285.1 > 156.1 | 653.9 | 7.1 |
| | Sulfadoxine | SDO | 311.1 > 156.1 | 676.9 | 7.6 |
| | Sulfamethoxazole | SMO | 254.1 > 156.1 | 685.1 | 7.8 |
| | Sulfaquinoxaline | SQO | 301.1 > 156.1 | 780.4 | 9.9 |
| Nitroimi-dazoles | 1-(2-Hydroxyethyl)-2-hydroxy-methyl-5-nitroimidazole | MNZ-OH | 188.1 > 123.1 | 419.5 | 1.4 |
| | 2-Hydroxymethyl-1-methyl-5-nitrimidazole | HMMNI | 158.1 > 140.1 | 453.1 | 2.0 |
| | Metronidazole | MNZ | 172.1 > 128.1 | 457.3 | 2.0 |
| | Dimetridazole | DMZ | 142.1 > 96.1 | 482.6 | 2.5 |
| | Ronidazole | RNZ | 201.1 > 55.1 | 493.3 | 2.8 |
| | 1-Methyl-2-(2'-hydroxy isopropyl)-5-nitroimidazole | IPZ-OH | 186.1 > 168.1 | 590.6 | 5.4 |
| | Ipronidazole | IPZ | 170.1 > 109.1 | 676.9 | 7.6 |
| Fluoro-quinolones | Ciprofloxacin | CIPRO | 332.2 > 245.1 | 601.0 | 5.7 |
| | Danofloxacin | DANO | 358.2 > 96.1 | 614.1 | 6.0 |
| | Enrofloxacin | ENRO | 360.2 > 316.2 | 625.2 | 6.3 |
| | Sarafloxacin | SARA | 386.2 > 342.2 | 666.2 | 7.4 |
| Quinolones | Oxolinic acid | OXA | 262.1 > 216.1 | 744.6 | 9.2 |
| Macrolides | Erythromycin | ERY | 734.5 > 158.1 | 833.3 | 10.9 |
| Dyes | Leucocrystal Violet | LCV | 374.4 > 358.1 | 660.3 | 7.2 |
| | Leucomalachite green | LMG | 331.1 > 316.1 | 983.2 | 13.5 |
| | Malachite Green | MG | 329.2 > 313.1 | 1180.8 | 16.3 |
| | Crystal Violet | CV | 372.4 > 356.1 | 1406.5 | 19.3 |
| | Brilliant Green | BG | 385.3 > 341.1 | 1572.6 | 21.5 |

Other advantages that are inherent to the invention are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A series of retention index standards for use in liquid chromatography, the series of retention index standards comprising two or more neutrally charged homologous compounds, each compound comprising at least one functional group bearing a positive charge and at least one functional group bearing a negative charge and each compound comprising an alkyl group having a different chain length, wherein each compound in the series has Formula (II):

(II)

where n is an integer from 0 to 23, and where each compound in the series has a different value for n.

2. The series of retention index standards according to claim 1, wherein the $SO_3^-$ is in the 3-position of the pyridine ring.

3. The series of retention index standards according to claim 1, wherein the liquid chromatography is liquid chromatography-mass spectrometry.

4. A method of identifying an analyte of interest comprising: introducing the analyte of interest together with a series of homologous retention index standards as defined in claim 1 into a liquid chromatography system; assigning a retention index value to the analyte of interest based on retention times and retention index values of the retention index standards; and, comparing spectral data and the retention index value of the analyte of interest to a library of spectral data and the retention index values for known compounds to identify the analyte of interest.

5. The method according to claim 4, wherein the $SO_3^-$ is in the 3-position of the pyridine ring.

6. The method according to claim 4, wherein the series of homologous retention index standards comprises from 4 to 16 homologues, and wherein each homologue comprises an alkyl group of different chain length.

7. The method according to claim 4, wherein the series of homologous compounds is co-injected with the analyte of interest into the liquid chromatography system.

8. The method according to claim 4, wherein assigning a retention index value to the analyte of interest comprises interpolating analyte retention times into a fitted curve of a plot of retention time vs. retention index value for the series of homologous retention index standards.

9. The method according to claim 4, wherein the analyte of interest is a toxin, pharmaceutical, drug of abuse, peptide, persistent environmental pollutant or food contaminant.

10. The method according claim 4, wherein the liquid chromatography system comprises a liquid chromatography-mass spectrometry system and the spectral data comprises mass spectrometry data.

* * * * *